United States Patent
Levak et al.

(10) Patent No.: US 9,880,157 B2
(45) Date of Patent: Jan. 30, 2018

(54) APPARATUS AND METHODS FOR SUPPRESSING USER-ALERTING ACTIONS

(71) Applicant: Pebble Technology, Corp., Redwood City, CA (US)

(72) Inventors: Henry Levak, San Mateo, CA (US); Melissa Sherman, Oakland, CA (US)

(73) Assignee: FITBIT, INC., San Francisco, CA (US)

( * ) Notice: Subject to any disclaimer, the term of this patent is extended or adjusted under 35 U.S.C. 154(b) by 0 days.

(21) Appl. No.: 15/072,856

(22) Filed: Mar. 17, 2016

(65) Prior Publication Data

US 2017/0273050 A1    Sep. 21, 2017

(51) Int. Cl.

| | |
|---|---|
| *H04W 68/00* | (2009.01) |
| *H04M 1/725* | (2006.01) |
| *H04W 4/14* | (2009.01) |
| *G01N 33/50* | (2006.01) |
| *G01N 15/14* | (2006.01) |
| *G01N 33/569* | (2006.01) |
| *G01N 33/574* | (2006.01) |
| *G06F 19/24* | (2011.01) |
| *G06K 9/00* | (2006.01) |
| *G06K 9/62* | (2006.01) |
| *G01N 15/00* | (2006.01) |
| *G06F 19/20* | (2011.01) |
| *G06F 19/26* | (2011.01) |

(52) U.S. Cl.
CPC ..... *G01N 33/5091* (2013.01); *G01N 15/1456* (2013.01); *G01N 33/56966* (2013.01); *G01N 33/56972* (2013.01); *G01N 33/574* (2013.01); *G01N 33/57492* (2013.01); *G06F 19/24* (2013.01); *G06K 9/00147* (2013.01); *G06K 9/6218* (2013.01); *G06K 9/6254* (2013.01); *G01N 2015/0065* (2013.01); *G06F 19/20* (2013.01); *G06F 19/26* (2013.01)

(58) Field of Classification Search
CPC ... H04W 68/005; H04W 4/14; H04M 1/7253; H04M 1/72566
See application file for complete search history.

(56) References Cited

U.S. PATENT DOCUMENTS 6,477,117 B1 * 11/2002 Narayanaswami .. G04G 13/026
368/224
8,572,486 B2 * 10/2013 Yach .................... G06Q 10/107
455/566

(Continued)

FOREIGN PATENT DOCUMENTS

| EP | 2504961 | 10/2012 |
|---|---|---|
| EP | 002655142-0001 | 3/2015 |
| EP | 002655118-0001 | 4/2015 |

OTHER PUBLICATIONS

Fitzpatrick, Jason, "How to Configure Do Not Disturb on Your iPhone and iPad", 4 pages. Published Mar. 26, 2015. Downloaded Nov. 12, 2015 from http://www.howtogeek.com/213089/how-to-configure-do-not-disturb-on-your-iphone-and-ipad/.

*Primary Examiner* — Marisol Figueroa
(74) *Attorney, Agent, or Firm* — Hogan Lovells US LLP

(57) ABSTRACT

Provided herein are apparatuses and methods related to a notification-affecting service on a wearable electronic device configured to set a quiet time mode preventing a user-alerting action selected from, for example, a haptic vibration, a visual effect, and an audible effect from alerting a user of the wearable electronic device.

20 Claims, 8 Drawing Sheets

(56) References Cited

U.S. PATENT DOCUMENTS

| | | | |
|---|---|---|---|
| D733,142 S | 6/2015 | Solomon et al. | |
| D743,278 S | 11/2015 | Solomon et al. | |
| D745,515 S | 12/2015 | Solomon et al. | |
| D750,625 S | 3/2016 | Solomon et al. | |
| 2006/0285533 A1* | 12/2006 | Divine | H04M 19/04 370/352 |
| 2009/0100256 A1* | 4/2009 | Fuccello | G06Q 10/109 713/100 |
| 2013/0040610 A1 | 2/2013 | Migicovsky et al. | |
| 2014/0012511 A1* | 1/2014 | Mensinger | A61B 5/72 702/19 |
| 2014/0282705 A1* | 9/2014 | Chatterjee | H04N 21/4882 725/33 |
| 2015/0126117 A1 | 5/2015 | Wong et al. | |
| 2015/0223033 A1 | 8/2015 | Migicovsky et al. | |
| 2015/0223034 A1 | 8/2015 | Migicovsky et al. | |
| 2015/0312403 A1* | 10/2015 | Youst | H04W 4/18 455/418 |
| 2015/0333302 A1 | 11/2015 | Johns et al. | |
| 2015/0334772 A1 | 11/2015 | Wong et al. | |
| 2016/0006859 A1* | 1/2016 | Janssen | H04M 1/72502 455/419 |
| 2016/0112866 A1* | 4/2016 | Hankins | H04W 8/22 455/418 |

\* cited by examiner

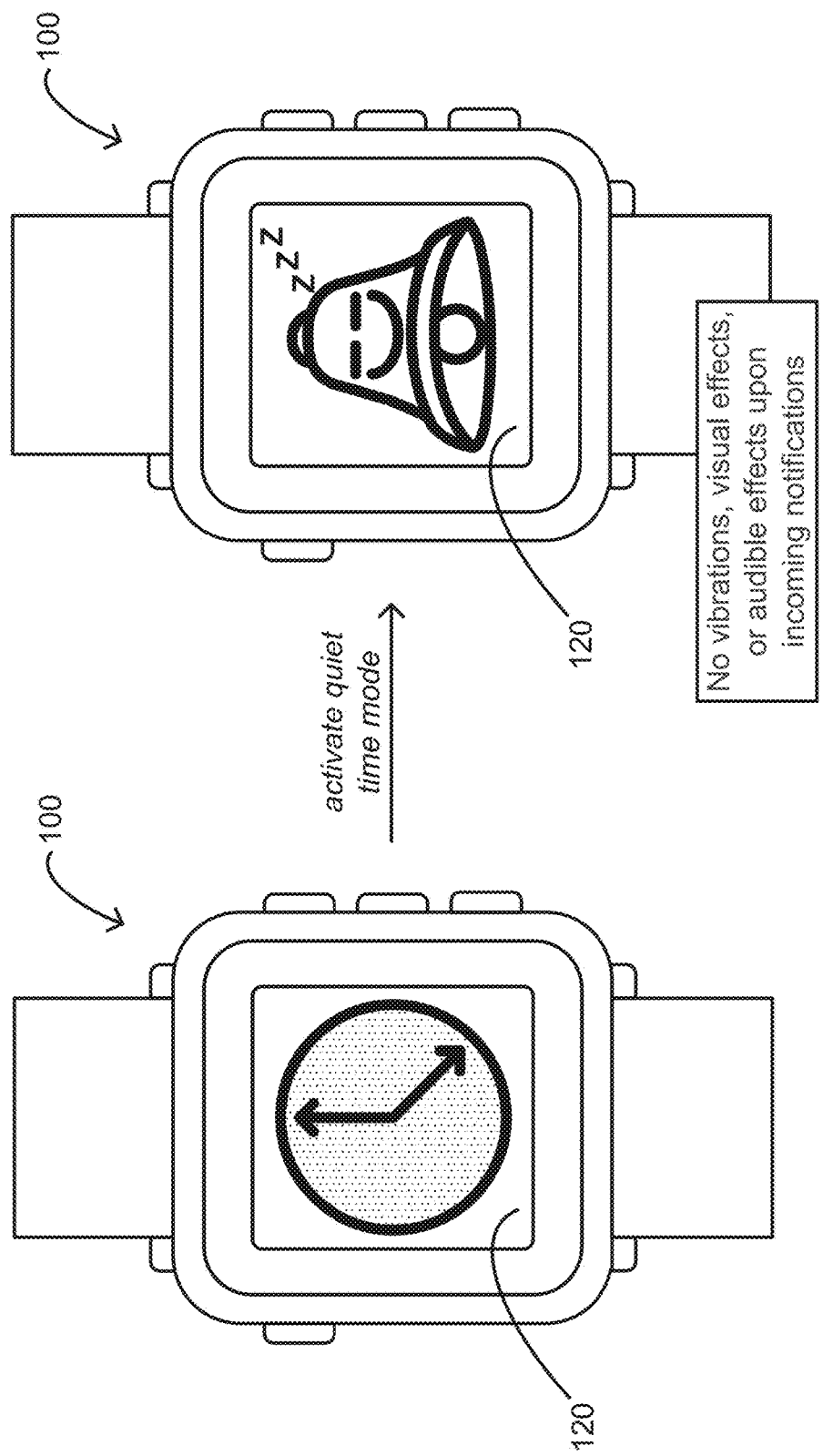

APPARATUS AND METHODS FOR SUPPRESSING USER-ALERTING ACTIONS

NOTICE OF COPYRIGHT

A portion of the disclosure of this patent document contains material that is subject to copyright protection. The copyright owner has no objection to the facsimile reproduction by anyone of the software engine and its modules, as it appears in the Patent and Trademark Office Patent file or records, but otherwise reserves all copyright rights whatsoever.

FIELD

Embodiments of the design provided herein generally relate to suppressing user-alerting actions corresponding to notifications on a wearable electronic device.

BACKGROUND

A wearable electronic device can receive notifications from a paired mobile electronic computing device. User-alerting actions on the wearable electronic device corresponding to incoming notifications can alert a user of the wearable electronic device. Such user-alerting actions can disturb the user if the user does not want to be alerted to incoming notifications.

SUMMARY

Provided herein are apparatuses and methods related to a notification-affecting service on a wearable electronic device configured to set a quiet time mode preventing a user-alerting action selected from, for example, a haptic vibration, a visual effect, and an audible effect from alerting a user of the wearable electronic device.

In some embodiments, an apparatus has a notification-affecting service resident in a memory of a wearable electronic device. The notification-affecting service can have one or more user interfaces to enable a user of the wearable electronic device to monitor a time synchronous application such as a timeline application or a calendar application. The wearable electronic device can have one or more processors configured to execute the notification-affecting service resident in the memory. The notification-affecting service can evaluate multiple events listed, logged, or scheduled in the time synchronous application. The notification-affecting service can also independently use an intelligence engine to determine whether to automatically set a quiet time mode, thereby preventing one or more user-alerting actions regarding a received notification. The user-alerting action can be a haptic vibration, a visual effect on a display screen of the wearable electronic device, such as turning on a back light of the wearable electronic device, and an audible sound effect emitted from the wearable electronic device. The received notification can be received by a wireless receiver circuit of the wearable electronic device. The received notification can be selected from any of the group consisting of calendar events notifications, incoming phone call notifications, mobile application generated notifications, SMS message notifications, and e-mail notifications. Portions of the notification-affecting service implemented in software are stored on the memory in an executable format by the one or more processors.

In some embodiments, a system has a mobile computing device and the foregoing wearable electronic device configured to pair with the mobile computing device.

In some embodiments, a method can enable a user of the foregoing wearable electronic device to monitor the time synchronous application with the notification-affecting service resident on the wearable electronic device.

DRAWINGS

The drawings refer to embodiments of the design provided herein in which:

FIG. 1B illustrates a wearable electronic device having a notification-affecting service in accordance with some embodiments.

Figure 1A:
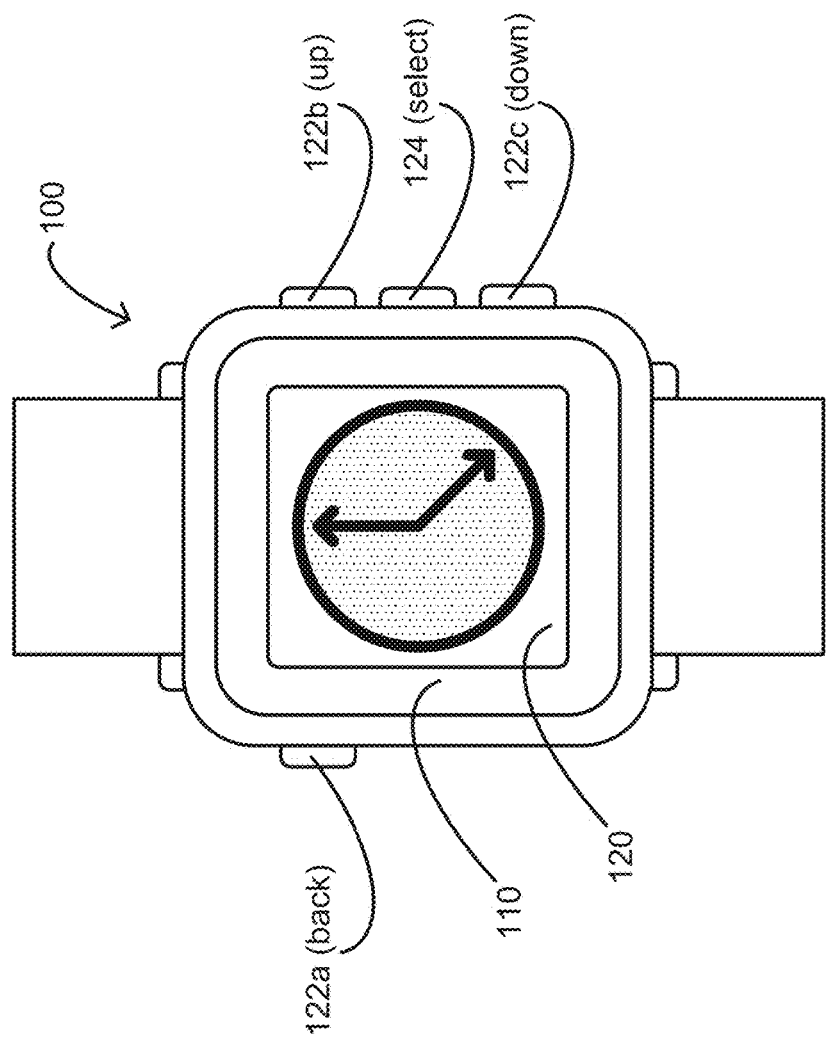
FIG. 1A illustrates a wearable electronic device in accordance with some embodiments.

While the design is subject to various modifications and alternative forms, specific embodiments thereof have been shown by way of example in the drawings and will herein be described in detail. The design should be understood to not be limited to the particular forms disclosed, but on the contrary, the intention is to cover all modifications, equivalents, and alternatives falling within the spirit and scope of the design.

DESCRIPTION

In the following description, numerous specific details are set forth, such as examples of specific data signals, named components, memory in a device, etc., in order to provide a thorough understanding of the present design. It will be apparent, however, to one of ordinary skill in the art that the present design can be practiced without these specific details. In other instances, well known components or methods have not been described in detail but rather in a block diagram in order to avoid unnecessarily obscuring the present design. Further, specific numeric references such as first driver, can be made. However, the specific numeric reference should not be interpreted as a literal sequential order but rather interpreted that the first notification is different than a second notification. Thus, the specific details set forth are merely exemplary. The specific details can be varied from and still be contemplated to be within the spirit and scope of the present design. The term coupled is defined as meaning connected either directly to the component or indirectly to the component through another component.

A wearable electronic device can receive notifications from a paired mobile electronic computing device. User-alerting actions on the wearable electronic device corresponding to incoming notifications can alert a user of the wearable electronic device. Such user-alerting actions can disturb the user if the user does not want to be alerted to incoming notifications.

Provided herein are apparatuses and methods related to a notification-affecting service on a wearable electronic device configured to set a quiet time mode preventing a user-alerting action selected from, for example, a haptic vibration, a visual effect, and an audible effect from alerting a user of the wearable electronic device. The quiet time mode is useful when the user does not want to be alerted to incoming notifications.

FIG. 1A illustrates a wearable electronic device 100 in accordance with some embodiments. As shown, the wearable electronic device 100 (e.g., smart watch) can have a display unit 110 housed in the wearable electronic device 100. The display unit 110 can have a display screen 120 to present one or more user interfaces to a user of the wearable electronic device 100. Depending upon the state of the wearable electronic device 100, the one or more user interfaces can include, but are not limited to, one or more user interfaces selected from a watch face (as shown), a launcher with cards corresponding to various applications on the wearable electronic device 100, and menus within the various applications. The wearable electronic device 100 can have, but is not limited to or required to have, one or more buttons such as buttons 122 and 124 for interacting with the one or more user interfaces. It should be understood that the display screen 120 can be a touchscreen obviating the buttons 122 and 124; however, the buttons 122 and 124 are shown at least for an expository purpose. As shown, navigating button 122a or back button 122a enables a user to go back to a previous user interface when pressed; navigating button 122b or up button 122b enables a user to, for example, scroll up through a user interface; and navigating button 122c or down button 122c enables a user to, for example, scroll down through a user interface. Using, for example, the navigating buttons 122a and 122b, the user can focus or highlight a user interface option. Once a desired user interface option is focused or highlighted, the user can select the user interface option using the select button 124.

FIG. 1B illustrates the wearable electronic device 100 having a notification-affecting service in accordance with some embodiments. As shown, the notification-affecting service (e.g., the notification-affecting service 210 of FIG. 2) can be activated setting a quiet time mode preventing a user-alerting action selected from, for example, a haptic vibration, a visual effect, and an audible effect from alerting a user of the wearable electronic device upon receiving an incoming notification.

Figure 2:
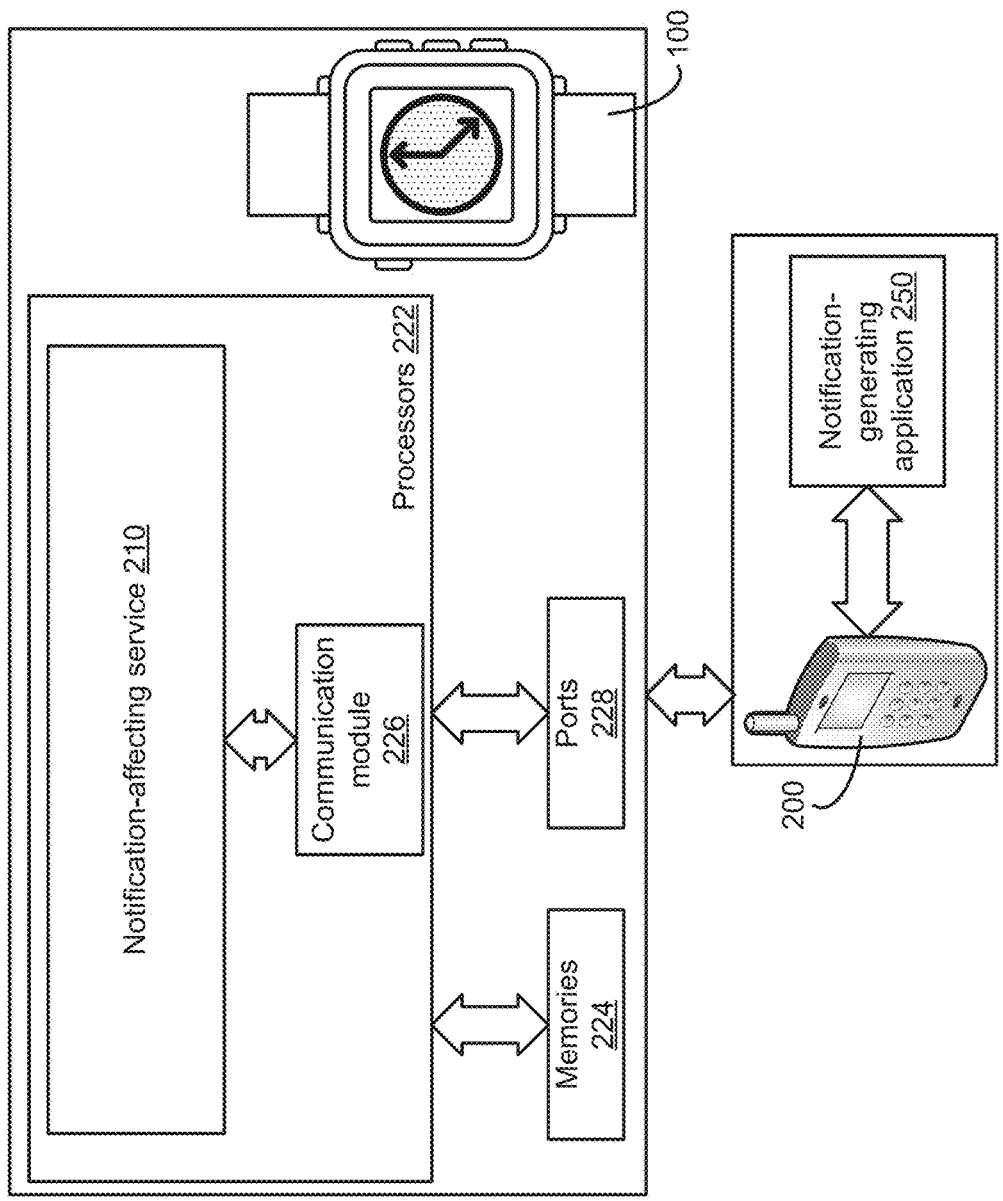
FIG. 2 illustrates a wearable electronic device having a notification-affecting service paired with a mobile computing device having a notification-generating application in accordance with some embodiments.

FIG. 2 illustrates the wearable electronic device 100 having the notification-affecting service 210 paired with a mobile computing device 200 having a notification-generating application 250 in accordance with some embodiments. As shown, the wearable electronic device 100 can have, but is not limited to, one or more processors 222 to execute instructions (e.g., suppressing user-alerting actions), memories 224 (e.g., a first memory 224a [not shown], a second memory 224b [not shown], etc.), and ports 228. The wearable electronic device 100 can also include a communication module 226 (e.g., wireless communication module) that can run on the processors 222 for communicating outside of the wearable electronic device 100. The notification-affecting service 210 can reside in the first memory 224a (not shown) of the wearable electronic device 100. In some embodiments, the notification-affecting service 210 is firmware and resides with other firmware for the wearable electronic device 100 in memories 224 such as the first memory 224a. As such, the notification-affecting service 210 can act globally on the wearable electronic device 100 and need not rely on, for example, each notification-generating application 250 on the mobile computing device 200 to implement a notification-affecting service for suppressing user-alerting actions that is specific to each notification-generating application 250. The notification-affecting service 210 resident in the first memory 224a of a wearable electronic device 100 can cooperate with one or more processors 222 to execute instructions such as suppressing user-alerting actions triggered by notifications from the notification-generating application 250.

The wearable electronic device 100 can communicate, via a wireless communication circuit, with the mobile computing device 200 (e.g., smart phone). The mobile computing device 200 can have one or more notification-generating applications 250 such as a time synchronous application. The one or more notification-generating applications 250 can include, but are not limited to, one or more notification-generating applications 250 selected from a timeline application, a calendar application, a phone call application, an SMS-message application, and an e-mail application. The one or more notification-generating applications 250 can trigger a user-alerting action (e.g., a haptic vibration by a vibrator, a visual effect on the display screen 120, an audible effect by a speaker, etc.) on the wearable electronic device 100 if the notification-affecting service 210 is not installed or in use on the wearable electronic device 100. The one or more notification-generating applications 250 can also trigger a user-alerting action on the wearable electronic device 100 if the notification-affecting service 210 is installed on the wearable electronic device 100 and if the notification-affecting service 210 is configured to allow the user-alerting action to alert the user.

In view of at least FIGS. 1A, 1B, and 2 and the description therefore, a notification-affecting service resident in a memory of a wearable electronic device can have one or more user interfaces enabling a user of the wearable electronic device to monitor a time synchronous application such as a timeline application or a calendar application. The wearable electronic device can have one or more processors for executing the notification-affecting service in the memory. The one or more user-alerting actions can be selected from, for example, a haptic vibration, a visual effect on a display screen of the wearable electronic device, such as turning on a back light of the wearable electronic device, and an audible sound effect emitted from the wearable electronic device. The notifications can correspond to calendar events notifications, incoming phone call notifications, SMS message notifications, or e-mail notifications.

Quiet Time Mode

If the notification-affecting service 210 is installed on the wearable electronic device 100, the notification-affecting service 210 can be configured to allow or disallow user-alerting actions. When the notification-affecting service 210 is configured to disallow user-alerting actions, the wearable electronic device 100 is said to be in quiet time mode. There are at least three quiet time modes for the wearable electronic device 100, namely 1) manual, 2) schedule aware, and 3) calendar aware.

The manual quiet time mode has no particular duration associated with it because it is activated and generally deactivated by the user. The manual quiet time mode can be activated by the user, for example, by a long-press on the back button 122a from the watch face or during an incoming notification. The manual quiet time mode can also be activated by the user in a settings menu (e.g., the Quiet Time Menu of FIG. 3B) for the notification-affecting service 210. Manual quiet time can also be deactivated by the user. An exception is when schedule-aware or calendar-aware quiet time mode is enabled and subsequently activated while the wearable electronic device 100 is in manual quiet time mode. When this occurs, the manual quiet time mode is automatically deactivated.

Settings for the schedule-aware quiet time mode enable the user to establish a quiet time-mode schedule that activates and deactivates quiet time mode (e.g., per an intelligence engine) when schedule-aware quiet time mode is enabled. The quiet time-mode schedule can be coincident with any one or more of the user's schedules selected from, for example, a work schedule, a leisure schedule, and a sleep schedule. For example, the user can specify a quiet time-mode schedule coincident with a work schedule such as a Monday-Friday or weekday schedule. The foregoing can be said to be a work schedule-aware setting. In such a work schedule-aware setting, quiet time mode can be automatically deactivated during a leisure schedule such as a Saturday-Sunday or weekend schedule. Alternatively, the user can specify a quiet time-mode schedule coincident with the leisure schedule. The foregoing can be said to be a leisure schedule-aware setting. In such a leisure schedule-aware setting, quiet time mode can be automatically deactivated during the work schedule. While such schedules can have preset start-and-stop time, the user can adjust the start-and-stop time as needed.

The calendar-aware quiet time mode automatically activates and deactivates quiet time mode (e.g., per an intelligence engine) for time-bound timeline-event pins and/or calendar events when the calendar-aware quiet time mode is enabled. For example, if the user has a pin in a calendar application for a meeting from 10:00 AM to 11:00 AM when the calendar-aware quiet time mode is enabled, the notification-affecting service 210 will activate quiet time mode at 10:00 AM and deactivate quiet time mode at 11:00 AM. The notification-affecting service 210 can give granular control to the user through a settings menu (e.g., the Quiet Time Menu of FIG. 3B) over the user-alerting actions for different notification-producing applications (e.g., the notification-generating application 250 on the mobile computing device 200 of FIG. 2) selected from the timeline application, the calendar application, a phone call application, an SMS message application, a social media site's application, and an e-mail application. In other words, the notification-affecting service 210 can give the user control through a settings menu over which notification-producing applications (e.g., the notification-generating application 250 on the mobile computing device 200 of FIG. 2) selected from, for example, the timeline application, the calendar application, a phone call application, an SMS message application, and an e-mail application to allow or disallow user-alerting actions.

Figure 3A:
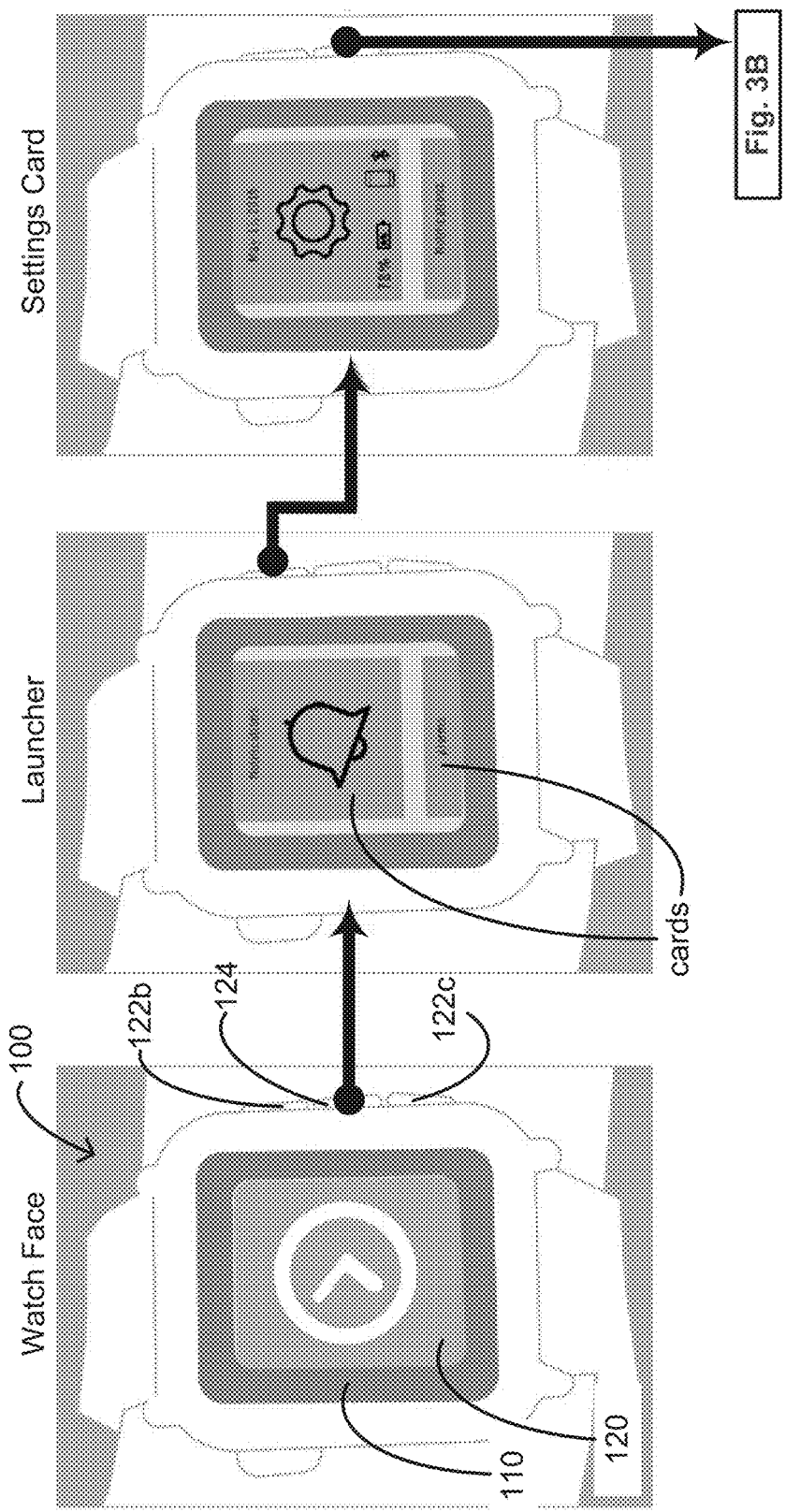
FIG. 3A illustrates navigation through one or more user interfaces to a notification-affecting service's settings in accordance with some embodiments.
Figure 3B:
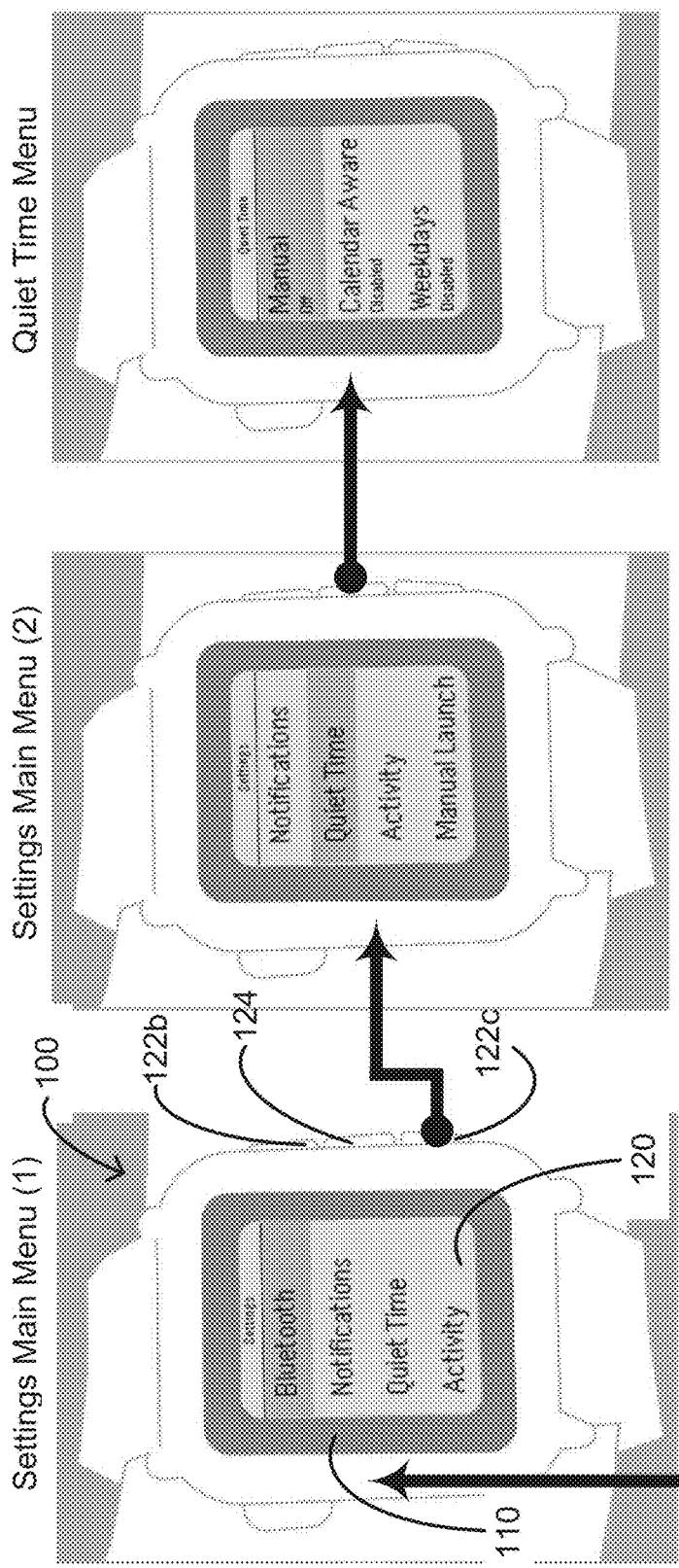
FIG. 3B illustrates navigation through one or more user interfaces to a notification-affecting service's settings in accordance with some embodiments.

When quiet time mode is activated under any of the manual, schedule-aware, or calendar-aware quiet time modes, the wearable electronic device 100, the wearable electronic device 100 does not vibrate or turn on the back light for incoming notifications, reminders, or phone calls, unless notifications for phone calls or certain contacts are expressly allowed in one or more interruptions-related settings (e.g., an interruption-related setting under the Quiet Time Menu of FIG. 3B). Notifications are still displayed without the back light, and the notifications do not go away until 1) the user clears or takes action on the notifications or 2) the notifications are automatically cleared. As such, notifications will "stack" and remain in a time-ordered stack until the user takes action on the notifications or the notifications are cleared. When quiet time mode is activated, an indicator is displayed about the stack of notifications, for example, in a screen header, to indicate the wearable electronic device is in the quiet time mode.

As such, the notification-affecting service can present the notifications on the display screen while the quiet time mode is active, but the notification-affecting service prevents the one or more user-alerting actions selected from the haptic vibration, the visual effect on the display screen, and the audible sound effect when the quiet time mode is active.

The stack of notifications may be divided into a first time-ordered stack of notifications and a second time-ordered stack of notifications with the second stack on top of the first stack. Notifications corresponding to reminders for events on the calendar application or pins in the timeline application can make up the second stack of notifications. The user can take action on the notifications in either stack directly on the wearable electronic device 100 or indirectly through the notification-generating application 250 on the mobile computing device 200. However, even without user intervention, the notifications in the second stack can be automatically cleared after a pre-determined expiration period (e.g., 10 mins). When a pre-determined expiration period (e.g., 10 minutes) has passed for one or more of the notifications in the second stack, the one or more notifications can be automatically removed from the second stack.

In view of at least the foregoing, the notification-affecting service can evaluate multiple events listed, logged, or scheduled in the time synchronous application. The notification service can independently use an intelligence engine to determine whether to automatically set a quiet time mode, thereby preventing one or more user-alerting actions. The received notification can be received by a wireless receiver circuit of the wearable electronic device. The received notification is selected from any of the group consisting of calendar events notifications, incoming phone call notifications, mobile application generated notifications, SMS message notifications, and e-mail notifications. The intelligence engine has logic trees for evaluating, for example, event types for events listed on the calendar application to determine whether a notification should be allowed to be communicated during a time period of any one of the events listed on the calendar application.

Activating Manual Quiet Time Mode

With respect to manual quiet time mode, it can be activated in at least three different ways: 1) The user can toggle the wearable electronic device 100 into the manual quiet time mode with a long-press (e.g., 2-second long press) on the back button 122a when the watch face is displayed on the display screen 120. 2) The user can also toggle the wearable electronic device 100 into the manual quiet time mode with a long-press (e.g., 2-second long press) on the back button 122a during an incoming notification. 3) The user can also toggle the wearable electronic device 100 into the manual quiet time mode from a settings menu (e.g., the Quiet Time Menu of FIG. 3B) for the notification-affecting service 210. However, the user cannot toggle the wearable electronic device 100 into the manual quiet time mode if the wearable electronic device 100 is already in a quiet time mode.

When the user toggles the wearable electronic device 100 into the manual quiet time mode with a long-press (e.g., 2-second long press) on the back button 122*a* from the watch face, the user will recognize the wearable electronic device 100 is in the manual quiet time mode from an indicator on the display screen 120. Such an indicator can be an animation for entering the manual quiet time mode. Subsequent to entering the manual quiet time mode in this way, the user can be returned to the watch face.

When the user receives a notification, the user can also toggle the wearable electronic device 100 into the manual quiet time mode with a long-press (e.g., 2-second long press) on the back button 122*a* during the incoming notification. Again, the user will recognize the wearable electronic device 100 is in the manual quiet time mode from an indicator on the display screen 120. Such an indicator can be an animation for entering the manual quiet time mode (e.g., the sleeping-bell animation of FIG. 1B). Subsequent to entering the manual quiet time mode in this way, the notification can remain focused or highlighted with an accessible notification action menu. In addition, another indicator can be displayed about the notification or a stack of notifications, for example, in a screen header, to indicate the wearable electronic device is in the manual quiet time mode.

As an alternative to toggling the wearable electronic device 100 into the manual quiet time mode with a long-press on the back button 122*a* during an incoming notification, the user can toggle the wearable electronic device 100 into the manual quiet time mode from the notification action menu. During an incoming notification, the notification can be focused or highlighted, and—using the select button 124—the user can select the notification and access the notification action menu. Depending upon the notification action menu's configuration, the user can use the up and/or down buttons (e.g., navigating buttons 122*b* and 122*c*) to navigate to an option for starting the manual quiet time mode. Upon the user selecting the option for starting the manual quiet time mode with the selected button 124, the wearable electronic device 100 can enter the manual quiet time mode. Again, the user will recognize the wearable electronic device 100 is in the manual quiet time mode from an indicator on the display screen 120. Such an indicator can be an animation for entering the manual quiet time mode (e.g., the sleeping-bell animation of FIG. 1B). Subsequent to entering the manual quiet time mode in this way, another indicator can be displayed about the notification or a stack of notifications, for example, in a screen header, to indicate the wearable electronic device 100 is in the manual quiet time mode.

The user can also toggle the wearable electronic device 100 into the manual quiet time mode from a settings menu (e.g., the Quiet Time Menu of FIG. 3B) for the notification-affecting service 210. Referencing FIG. 3A, from the watch face on the display screen 120 of the wearable electronic device 100, the user can press the select button 124 to activate a launcher (e.g., the Launcher of FIG. 3A) with cards corresponding to various applications on and settings for the wearable electronic device 100. Depending upon the launcher's configuration, the user can use the up and/or down buttons (e.g., navigating buttons 122*b* and 122*c*) to flip the cards and, thereby, navigate to the settings menu (e.g., the Quiet Time Menu of FIG. 3B) for the notification-affecting service 210 through a corresponding settings card. Alternatively, as shown in FIG. 3B, the settings menu for the notification-affecting service 210 can be incorporated into a main settings menu (e.g., Settings Menu (1) and (2)) for the wearable electronic device 100, which can be accessed through a corresponding settings card (e.g., Settings Card of FIG. 3A). Upon the user selecting the settings menu for notification-affecting service 210 with the select button 124, the user can use the up and/or down buttons (e.g., navigating buttons 122*b* and 122*c*) to navigate to an option in the settings menu to toggle the wearable electronic device 100 into the manual quiet time mode. Again, the user will recognize the wearable electronic device 100 is in the manual quiet time mode from one or more indicators presented on the display screen 120.

Enabling/Disabling and Activating Schedule-Aware Quiet Time Mode

With respect to schedule-aware quiet time mode, it can be enabled and activated in at least the following way: The user can enable and optionally adjust the schedule-aware quiet time mode from a settings menu (e.g., the Quiet Time Menu of FIG. 3B) for the notification-affecting service 210, and the wearable electronic device 100 can activate the schedule-aware quiet time mode in accordance with a preset or user-adjusted schedule such as a work schedule, a leisure schedule, or a sleep schedule.

Enabling a service or service feature such as the schedule-aware quiet time mode permits the service or service feature to run in a background process to determine when one or more conditions are met (e.g., start or end of a work schedule). Disabling a service or service feature such as the schedule-aware quiet time mode forbids the service or service feature to run in a background process. When the service or service feature is enabled and the one or more conditions are met (e.g., the start or end of the work schedule), the service or service feature activates or deactivates. Following on the foregoing example, the schedule-aware quiet time mode activates, and, thereby, suppresses user-alerting actions, in accordance with the start of the work schedule. Continuing with the foregoing example, the schedule-aware quiet time mode deactivates, and, thereby, allows user-alerting actions, in accordance with the end of the work schedule.

The user can toggle the wearable electronic device 100 into or out of the schedule-aware quiet time mode from the settings menu (e.g., the Quiet Time Menu of FIG. 3B) for the notification-affecting service 210. As such, the user can enable or disable the schedule-aware quiet time mode from the settings menu. Referencing FIG. 3A, from the watch face on the display screen 120 of the wearable electronic device 100, the user can press the select button 124 to activate the launcher (e.g., the Launcher of FIG. 3A). Depending upon the launcher's configuration, the user can use the up and/or down buttons (e.g., navigating buttons 122*b* and 122*c*) to flip the cards and, thereby, navigate to the settings menu (e.g., the Quiet Time Menu of FIG. 3B) for the notification-affecting service 210. Alternatively, as shown in FIG. 3B, the settings menu for the notification-affecting service 210 can be incorporated into a main settings menu (e.g., Settings Menu (1) and (2)) for the wearable electronic device 100, which can be accessed through a corresponding settings card (e.g., Settings Card of FIG. 3A). Upon the user selecting the settings menu with the select button 124, the user can use the up and/or down buttons (e.g., navigating buttons 122*b* and 122*c*) to navigate to an option in the settings menu to toggle the wearable electronic device 100 into or out of the schedule-aware quiet time mode to respectively enable or disable the schedule-aware quiet time mode. A default or preset schedule with preset start-and-stop times can be user-adjusted from the settings menu for the notification-affecting service 210. When the schedule-aware quiet time mode is enabled, the wearable electronic device 100 can activate the schedule-aware quiet time mode and, thereby, suppress user-alerting actions, in accordance with a scheduled start time. The wearable electronic device 100 can also deactivate the schedule-aware quiet time mode and, thereby, allow user-alerting actions, in accordance with a scheduled stop time.

If the wearable electronic device 100 is in the manual quiet time mode or the calendar-aware quiet time mode when the schedule-aware quiet time mode is enabled and subsequently activated, the wearable electronic device 100 will deactivate the manual quiet time mode or the calendar-aware quiet time mode at least until the scheduled stop time for the schedule-aware quiet time mode.

In view of at least the foregoing, the notification-affecting service can be i) on a scheduled setting, thereby affecting communication of any notifications based on a day of the week and time of day; ii) on a calendar-aware setting, thereby affecting some or all the notifications; and iii) manually turned off allowing notifications to be freely communicated via the one or more user-alerting actions to a user of the wearable electronic device. The notification-affecting service can determine whether to automatically set a quiet time mode for multiple discreet blocks of time throughout the calendar day preventing the one or more user-alerting actions for at least some or all notifications throughout the day in either the calendar-aware setting or the scheduled setting.

Enabling/Disabling and Activating Calendar-Aware Quiet Time Mode

With respect to calendar-aware quiet time mode, it can be enabled and activated in at least the following way: The user can enable the calendar-aware quiet time mode from a settings menu (e.g., the Quiet Time Menu of FIG. 3B) for the notification-affecting service 210, and the wearable electronic device 100 can activate the calendar-aware quiet time mode in accordance with time-bound timeline-event pins and/or calendar events.

Enabling a service or service feature such as the calendar-aware quiet time mode permits the service or service feature to run in a background process to determine when one or more conditions are met (e.g., start or end of a calendar event). Disabling a service or service feature such as the calendar-aware quiet time mode forbids the service or service feature to run in a background process. When the service or service feature is enabled and the one or more conditions are met (e.g., the start or end of the calendar event), the service or service feature activates or deactivates. Following on the foregoing example, the calendar-aware quiet time mode activates, and, thereby, suppresses user-alerting actions, in accordance with the start of the calendar event. Continuing with the foregoing example, the calendar-aware quiet time mode deactivates, and, thereby, allows user-alerting actions, in accordance with the end of the calendar event.

As described for the schedule-aware quiet time mode, the user can likewise toggle the wearable electronic device 100 into or out of the calendar-aware quiet time mode from the settings menu (e.g., the Quiet Time Menu of FIG. 3B) for the notification-affecting service 210. As such, the user can enable or disable the calendar-aware quiet time mode from the settings menu. Upon the user selecting the settings menu from the launcher or from the main settings menu with the select button 124 as described herein, the user can use the up and/or down buttons (e.g., navigating buttons 122b and 122c) to navigate to an option in the settings menu to toggle the wearable electronic device 100 into or out of the calendar-aware quiet time mode to respectively enable or disable the calendar-aware quiet time mode. When the calendar-aware quiet time mode is enabled, the wearable electronic device 100 can activate the calendar-aware quiet time mode and, thereby, suppress user-alerting actions, in accordance with start times for time-bound timeline-event pins and/or calendar events. The wearable electronic device 100 can also deactivate the calendar-aware quiet time mode and, thereby, allow user-alerting actions, in accordance with stop times for time-bound timeline-event pins and/or calendar events.

If the wearable electronic device 100 is in the manual quiet time mode when the calendar-aware quiet time mode is enabled and subsequently activated, the wearable electronic device 100 will deactivate the manual quiet time mode at least until the stop times for the instant time-bound timeline-event pin and/or calendar event. That said, the calendar-aware quiet time mode is not configured to override a concurrent, enabled schedule-aware quiet time mode.

In view of at least the foregoing, the notification-affecting service can be i) on a scheduled setting, thereby affecting communication of any notifications based on a day of the week and time of day; ii) on a calendar-aware setting, thereby affecting some or all the notifications; and iii) manually turned off allowing notifications to be freely communicated via the one or more user-alerting actions to a user of the wearable electronic device. The notification-affecting service can determine whether to automatically set a quiet time mode for multiple discreet blocks of time throughout the calendar day preventing the one or more user-alerting actions for at least some or all notifications throughout the day in either the calendar-aware setting or the scheduled setting.

The wearable electronic device can also automatically enter the quiet time mode or not during a time period for any one of the multiple events listed, logged, or scheduled in the time synchronous application including events on the calendar application or pins in the timeline application. The wearable electronic device automatically not entering the quiet time mode can depend upon event types for events listed on the calendar application or pin types for pins in the timeline application as described herein.

In view of at least Activating Manual Quiet Time Mode, Enabling/Disabling and Activating Schedule-Aware Quiet Time Mode, and Enabling/Disabling and Activating Calendar-Aware Quiet Time Mode, one or more user interfaces can present multiple notification-service settings on the display screen to enable the user to choose one or more user-selectable settings. The one or more user-selectable settings can be selected from i) a manual setting configured to enable the user to enable or disable the user-alerting actions as desired, ii) a calendar-aware setting configured to automatically enter the quiet time mode during a time period for any one of the multiple events listed, logged, or scheduled in the time synchronous application including events on the calendar application, and iii) a work schedule-aware setting configured to enable the user to set different behaviors for a work schedule such as a work week schedule and a leisure schedule such as a weekend schedule. The one or more users interfaces can present an option to the user to set both a start time and end time for the leisure schedule.

Manually Deactivating Quiet Time Mode

As described above, when either one or both of the schedule-aware and calendar-aware quiet time modes are enabled, the wearable electronic device 100 can automatically activate and/or deactivate the foregoing quiet time modes. For example, the wearable electronic device 100 can activate and/or deactivate the schedule-aware quiet time mode in accordance with a preset or user-adjusted schedule such as a work schedule, a leisure schedule, or a sleep schedule. For example, the wearable electronic device 100 can activate and/or deactivate the calendar-aware quiet time mode in accordance with time-bound timeline-event pins and/or calendar events. In some embodiments, the schedule-aware and calendar-aware quiet time modes can be enabled on the wearable electronic device 100 at the same time, but only one of the foregoing quiet time modes or the manual quiet time mode can be active at the same time. As such, the notification-affecting service 210 enables the user to manually deactivate any quiet time mode selected from the schedule-aware quiet time mode, calendar-aware quiet time mode, and manual quiet time mode.

With respect to deactivating quiet time mode, it can be deactivated in at least three different ways: 1) The user can toggle the wearable electronic device 100 out of the quiet time mode, and, thereby, deactivate the quiet time mode with a long-press (e.g., 2-second long press) on the back button 122*a* when the watch face is displayed on the display screen 120. 2) The user can also toggle the wearable electronic device 100 out of the quiet time mode with a long-press (e.g., 2-second long press) on the back button 122*a* during an incoming notification. 3) The user can also toggle the wearable electronic device 100 out of the quiet time mode from a settings menu (e.g., the Quiet Time Menu of FIG. 3B) for the notification-affecting service 210.

When the user toggles the wearable electronic device 100 out of, and, thereby deactivates, the schedule-aware quiet time mode, the calendar-aware quiet time mode, or the manual quiet time mode with a long-press (e.g., 2-second long press) on the back button 122*a* from the watch face, the user will recognize the wearable electronic device 100 is no longer in the quiet time mode from an indicator on the display screen 120. Such an indicator can be an animation for exiting the quiet time mode. Subsequent to exiting the quiet time mode in this way, the user can be returned to the watch face.

When the user receives a notification, the user can also toggle the wearable electronic device 100 out of, and, thereby deactivate, the schedule-aware quiet time mode, the calendar-aware quiet time mode, or the manual quiet time mode with a long-press (e.g., 2-second long press) on the back button 122*a* during the incoming notification. Again, the user will recognize the wearable electronic device 100 is no longer in the quiet time mode from an indicator on the display screen 120. Such an indicator can be an animation for exiting the quiet time mode. Subsequent to exiting the quiet time mode in this way, the notification can remain focused or highlighted with an accessible notification action menu. In addition, absence of the quiet time-mode indicator displayed about the notification or a stack of notifications, for example, in the screen header, indicates the wearable electronic device 100 is no longer in the manual quiet time mode.

As an alternative to toggling the wearable electronic device 100 out of the schedule-aware quiet time mode, the calendar-aware quiet time mode, or the manual quiet time mode with a long-press on the back button 122*a* during an incoming notification, the user can toggle the wearable electronic device 100 out of, and, thereby deactivate, the quiet time mode from the notification action menu. During an incoming notification, the notification can be focused or highlighted, and—using the select button 124—the user can select the notification and access the notification action menu. Depending upon the notification action menu's configuration, the user can use the up and/or down buttons (e.g., navigating buttons 122*b* and 122*c*) to navigate to an option for stopping the quiet time mode. Upon the user selecting the option for stopping the quiet time mode with the selected button 124, the wearable electronic device 100 can exit the quiet time mode. Again, the user will recognize the wearable electronic device 100 is no longer in the quiet time mode from an indicator on the display screen 120. Such an indicator can be an animation for exiting the quiet time mode. Subsequent to exiting the quiet time mode in this way, absence of the quiet time-mode indicator displayed about the notification or a stack of notifications, for example, in the screen header, indicates the wearable electronic device 100 is no longer in the quiet time mode.

Figure 4:
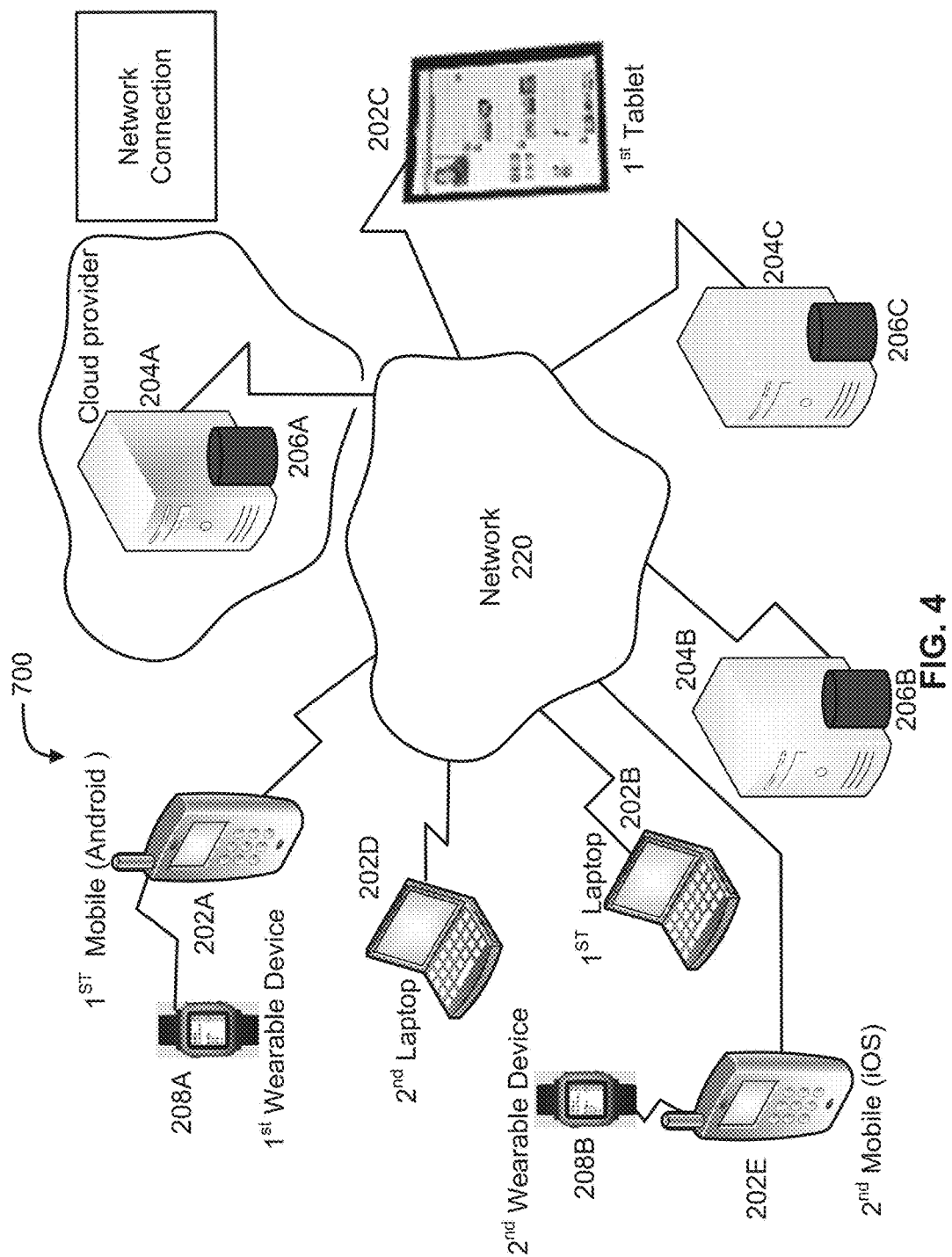
FIG. 4 illustrates two or more wearable electronic devices communicating with other electronic devices on a network in accordance with some embodiments.

The user can also toggle the wearable electronic device 100 out of the schedule-aware quiet time mode, the calendar-aware quiet time mode, or the manual quiet time mode from the settings menu (e.g., the Quiet Time Menu of FIG. 3B) for the notification-affecting service 210. Upon the user selecting the settings menu from the launcher or from the main settings menu with the select button 124 as described herein, the user can use the up and/or down buttons (e.g., navigating buttons 122*b* and 122*c*) to navigate to an option in the settings menu to toggle the wearable electronic device 100 out of the quiet time mode. Again, the user will recognize the wearable electronic device 100 is out of the quiet time mode from one or more indicators and/or the absence of one or more indicators presented on the display screen 120, Network FIG. 4 illustrates two or more wearable electronic devices communicating with other electronic devices on a network in accordance with some embodiments. The wearable electronic devices 208A, 208B may remotely access and/or communicate with other devices on a network in accordance with some embodiments. The network environment 700 has a communications network 220 that connects server computing systems 204A through 204C, and at least one or more client computing systems 202A to 202E, as well as 208A and 208B. As shown, there may be many server computing systems 204A through 204C and many client computing systems 202A to 202E, as well as 208A and 208B connected to each other via the network 220, which may be, for example, the Internet. The cloud-based server 204A can be coupled to two or more wearable electronic devices 208A and 208B and can bi-directionally communicate with the two or more mobile electronic devices 202A, 202B.

Referring back to FIG. 4, note, that alternatively the network 220 might be or include one or more of: an optical network, a cellular network, the Internet, a Local Area Network (LAN), Wide Area Network (WAN), satellite link, fiber network, cable network, or a combination of these and/or others. It is to be further appreciated that the use of the terms client computing system and server computing system is for clarity in specifying who generally initiates a communication (the client computing system) and who responds (the server computing system). No hierarchy is implied unless explicitly stated. Both functions may be in a single communicating device, in which case the client-server and server-client relationship may be viewed as peer-to-peer. Thus, if two systems such as the client computing system 202A and the server computing system 204A can both initiate and respond to communications, their communication may be viewed as peer-to-peer. Likewise, communications between the server computing systems 204A and 204-B, and the client computing systems 202A and 202C may be viewed as peer-to-peer if each such communicating device is capable of initiation and response to communication. Additionally, server computing systems 204A-204C also have circuitry and software to communication with each other across the network 220. One or more of the server computing systems 204A to 204C may be associated with a database such as, for example, the databases 206A to 206C. Each server may have one or more instances of a virtual server running on that physical server and multiple virtual instances may be implemented by the design. A firewall may be established between a client computing system 202C and the network 220 to protect data integrity on the client computing system 202C. Each server computing system 204A-204C may have one or more firewalls.

A cloud provider service can install and operate application software in the cloud and users can access the software service from the client devices. Cloud users who have a site in the cloud may not solely manage the cloud infrastructure and platform where the application runs. Thus, the servers and databases may be shared hardware where the user is given a certain amount of dedicate use of these resources. The user's cloud-based site is given a virtual amount of dedicated space and bandwidth in the cloud. Cloud applications can be different from other applications in their scalability, which can be achieved by cloning tasks onto multiple virtual machines at run-time to meet changing work demand. Load balancers distribute the work over the set of virtual machines. This process is transparent to the cloud user, who sees only a single access point.

The cloud-based remote access is coded to utilize a protocol, such as Hypertext Transfer Protocol (HTTP), to engage in a request and response cycle with both a mobile device application resident on a client device as well as a web-browser application resident on the client device. The cloud-based remote access for a wearable electronic device, can be accessed by a mobile device, a desktop, a tablet device, and other similar devices, anytime, anywhere. Thus, the cloud-based remote access to a wearable electronic device hosted on a cloud-based provider site is coded to engage in 1) the request and response cycle from all web browser based applications, 2) SMS/twitter based request and response message exchanges, 3) the request and response cycle from a dedicated on-line server, 4) the request and response cycle directly between a native mobile application resident on a client device and the cloud-based remote access to a wearable electronic device, and 5) combinations of these.

In an embodiment, the server computing system 204A may include a server engine, a web page management component, a content management component, and a database management component. The server engine performs basic processing and operating system level tasks. The web page management component handles creation and display or routing of web pages or screens associated with receiving and providing digital content and digital advertisements. Users may access the server-computing device by means of a URL associated therewith. The content management component handles most of the functions in the embodiments described herein. The database management component includes storage and retrieval tasks with respect to the database, queries to the database, and storage of data.

An embodiment of a server computing system to display information, such as a web page, etc. is discussed. An application including any program modules, apps, services, processes, and other similar software executable when executed on the server computing system 204A, causes the server computing system 204A to display windows and user interface screens on a portion of a media space, such as a web page. A user via a browser from the client computing system 202A may interact with the web page, and then supply input to the query/fields and/or service presented by a user interface of the application. The web page may be served by a web server computing system 204A on any Hypertext Markup Language (HTML) or Wireless Access Protocol (WAP) enabled client computing system 202A or any equivalent thereof. For example, the client mobile computing system 202A may be a wearable electronic device, smart phone, a touch pad, a laptop, a netbook, etc. The client computing system 202A may host a browser, a mobile application, and/or watch specific application to interact with the server computing system 204A. Each application has a code scripted to perform the functions that the software component is coded to carry out such as presenting fields and icons to take details of desired information. Algorithms, routines, and engines within the server computing system 204A take the information from the presenting fields and icons and put that information into an appropriate storage medium such as a database. A comparison wizard is scripted to refer to a database and make use of such data. The applications may be hosted on the server computing system 204A and served to the browser of the client computing system 202A. The applications then serve pages that allow entry of details and further pages that allow entry of more details.

Computing System

Figure 5:
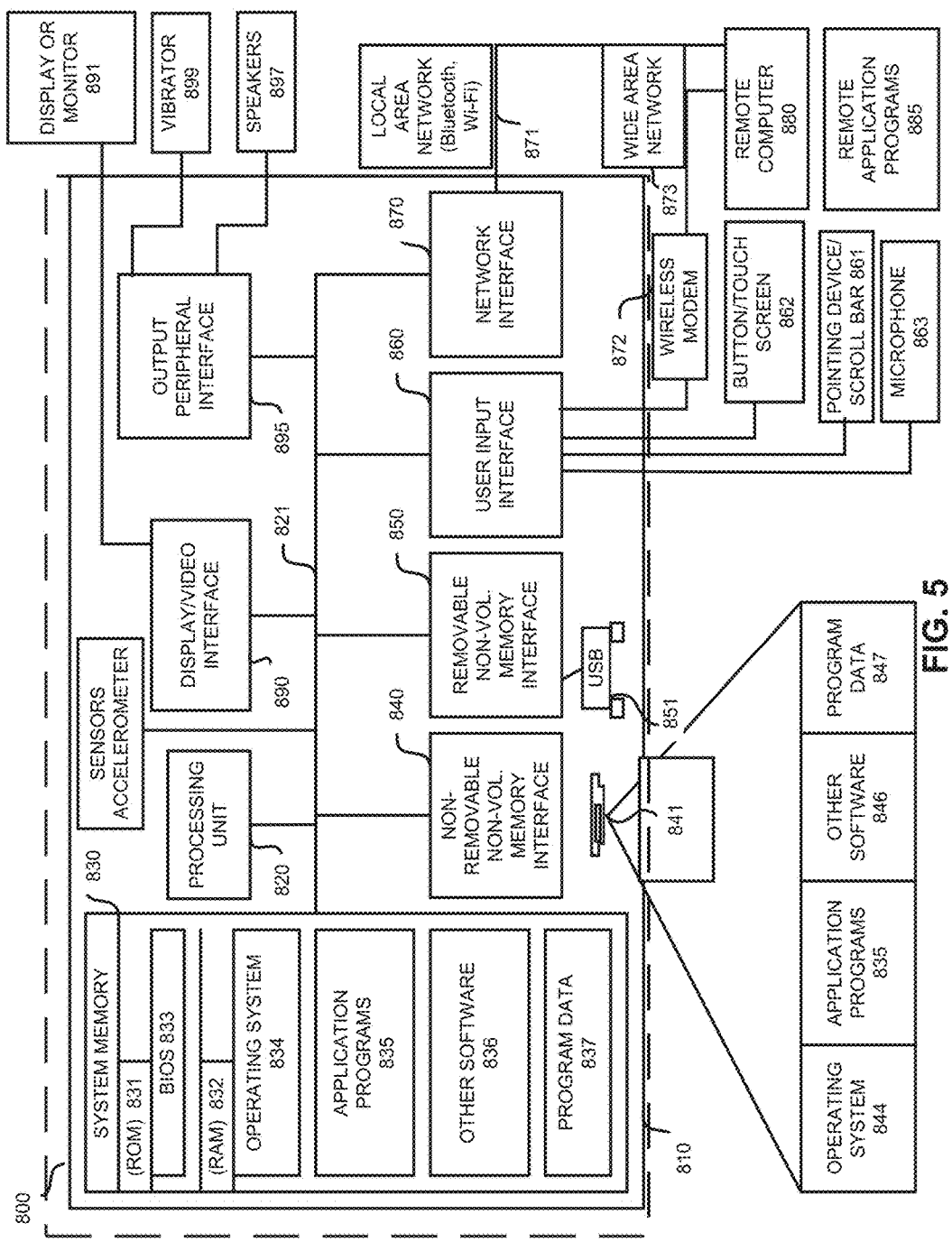
FIG. 5 illustrates a computing system that can be part of one or more of the wearable electronic devices in accordance with some embodiments.

FIG. 5 illustrates a computing system that can be part of one or more of the wearable electronic devices in accordance with some embodiments. With reference to FIG. 5, components of the computing system 810 may include, but are not limited to, a processing unit 820 having one or more processing cores, a system memory 830, and a system bus 821 that couples various system components including the system memory to the processing unit 820. The system bus 821 may be any of several types of bus structures including a memory bus or memory controller, a peripheral bus, and a local bus using any of a variety of bus architectures.

Computing system 810 typically includes a variety of computing machine-readable media. Computing machine-readable media can be any available media that can be accessed by computing system 810 and includes both volatile and nonvolatile media, removable and non-removable media. By way of example, and not limitation, computing machine-readable mediums uses include storage of information, such as computer readable instructions, data structures, other executable software or other data. Computer storage mediums include, but are not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other tangible medium which can be used to store the desired information and which can be accessed by computing device 800. Transitory media such as wireless channels are not included in the machine-readable media. Communication media typically embodies computer readable instructions, data structures, other executable software, or other transport mechanism and includes any information delivery media. As an example, some clients on network 220 of FIG. 4 may not have any optical or magnetic storage.

The system memory 830 includes computer storage media in the form of volatile and/or nonvolatile memory such as read only memory (ROM) 831 and random access memory (RAM) 832. A basic input/output system 833 (BIOS), containing the basic routines that help to transfer information between elements within computing system 810, such as during start-up, is typically stored in ROM 831. RAM 832 typically contains data and/or software that are immediately accessible to and/or presently being operated on by processing unit 820. By way of example, and not limitation, FIG. 5 illustrates that RAM can include a portion of the operating system 834, other executable software 836, and program data 837.

The computing system 810 may also include other removable/non-removable volatile/nonvolatile computer storage media. By way of example only, FIG. 5 illustrates a solid-state memory 841. Other removable/non-removable, volatile/nonvolatile computer storage media that can be used in the exemplary operating environment include, but are not limited to, USB drives and devices, flash memory cards, solid state RAM, solid state ROM, and the like. The solid-state memory 841 is typically connected to the system bus 821 through a non-removable memory interface such as interface 840, and USB drive 851 is typically connected to the system bus 821 by a removable memory interface, such as interface 850.

As an example, the computer readable storage medium 841 stores Operating System software for smart watches to cooperate with both Android OS and iOS.

The drives and their associated computer storage media discussed above and illustrated in FIG. 5, provide storage of computer readable instructions, data structures, other executable software and other data for the computing system 810. In FIG. 5, for example, the solid state memory 841 is illustrated for storing operating system 844, other executable software 846, and program data 847. Note that these components can either be the same as or different from operating system 834, other executable software 836, and program data 837. Operating system 844, other executable software 846, and program data 847 are given different numbers here to illustrate that, at a minimum, they are different copies. In an example, the operating system, Pebble OS, can be a customized Free RTOS kernel that can communicate with Android and iOS applications using Bluetooth, Wi-Fi, cellular or other communication methodology.

A user may enter commands and information into the computing system 810 through input devices such as a keyboard, touchscreen, or even push button input component 862, a microphone 863, a pointing device and/or scrolling input component 861, such as a mouse, trackball or touch pad. The microphone 863 may cooperate with speech recognition software. These and other input devices are often connected to the processing unit 820 through a user input interface 860 that is coupled to the system bus, but may be connected by other interface and bus structures, such as a parallel port, game port or a universal serial bus (USB). A display monitor 891 or other type of display screen device is also connected to the system bus 821 via an interface, such as a display and video interface 890. In addition to the monitor, computing devices may also include other peripheral output devices such as speakers 897, a vibrator 899, and other output device, which may be connected through an output peripheral interface 890.

The computing system 810 may operate in a networked environment using logical connections to one or more remote computers/client devices, such as a remote computing device 880. The remote computing device 880 may be a wearable electronic device, a personal computer, a hand-held device, a server, a router, a network PC, a peer device or other common network node, and typically includes many or all of the elements described above relative to the computing system 810. The logical connections depicted in FIG. 4 include a local area network (LAN) 871 and a wide area network (WAN) 873, but may also include other networks. Such networking environments are commonplace in offices, enterprise-wide computer networks, intranets and the Internet. A browser application may be resident on the computing device and stored in the memory.

When used in a LAN networking environment, the computing system 810 is connected to the LAN 871 through a network interface or adapter 870, which can be a Bluetooth or Wi-Fi adapter. When used in a WAN networking environment, the computing system 810 typically includes a modem 872, e.g., a wireless network, or other means for establishing communications over the WAN 873, such as the Internet. The wireless modem 872, which may be internal or external, may be connected to the system bus 821 via the user-input interface 860, or other appropriate mechanism. In a networked environment, other software depicted relative to the computing system 810, or portions thereof, may be stored in the remote memory storage device. By way of example, and not limitation, FIG. 5 illustrates remote application programs 885 as residing on remote computing device 880. It will be appreciated that the network connections shown are exemplary and other means of establishing a communications link between the computing devices may be used.

As discussed, the computing system may include a processor, a memory, a built in battery to power the computing device, an AC power input to charge the battery, a display screen, a built-in Wi-Fi circuitry to wirelessly communicate with a remote computing device connected to network.

It should be noted that the present design can be carried out on a computing system such as that described with respect to FIG. 5. However, the present design can be carried out on a server, a computing device devoted to message handling, or on a distributed system in which different portions of the present design are carried out on different parts of the distributed computing system.

Another device that may be coupled to bus 811 is a power supply such as a battery and Alternating Current adapter circuit. As discussed above, the DC power supply may be a battery, a fuel cell, or similar DC power source that needs to be recharged on a periodic basis. The wireless communication module 872 may employ a Wireless Application Protocol to establish a wireless communication channel. The wireless communication module 872 may implement a wireless networking standard.

Examples of mobile computing devices may be a laptop computer, a smart phone, a personal digital assistant, or other similar device with on board processing power and wireless communications ability that is powered by a Direct Current (DC) power source that supplies DC voltage to the mobile device and that is solely within the mobile computing device and needs to be recharged on a periodic basis, such as a fuel cell or a battery.

Notification-Affecting Service Methods

Figure 6:
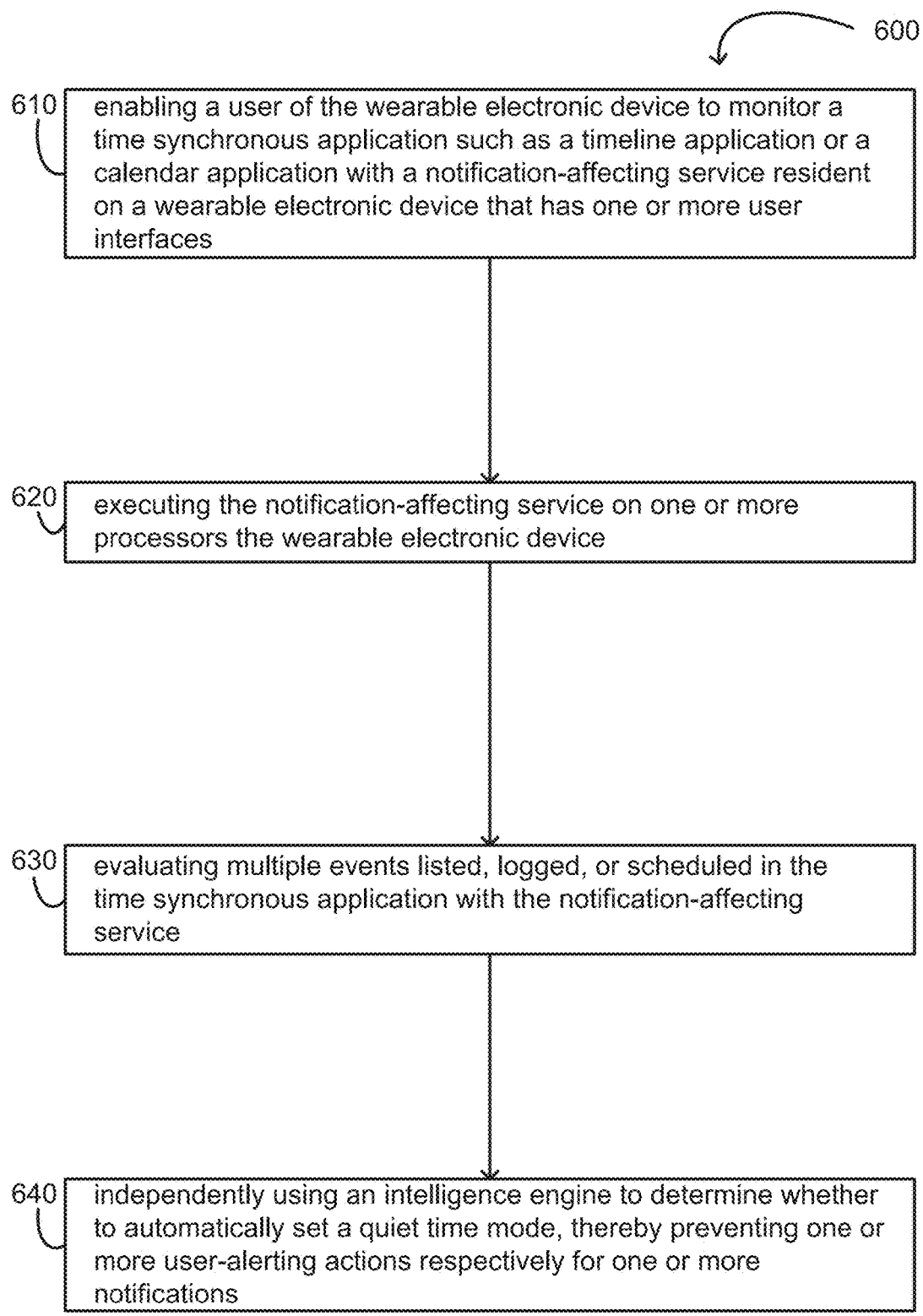
FIG. 6 illustrates a method 600 with respect to a notification-affecting service in accordance with some embodiments.

FIG. 6 illustrates a method 600 with respect to a notification-affecting service in accordance with some embodiments. The method and the steps thereof can be performed out of literal order when logically possible. Data and routines of the methods can be stored on a memory of the wearable electronic device 100, a memory of the mobile computing device 200, or any combination thereof. The steps of the methods can be executed on the wearable electronic device 100, the mobile computing device 200, or any combination thereof when logically possible.

FIG. 6 illustrates the method 600 having a first step 610 of enabling a user of the wearable electronic device to monitor a time synchronous application such as a timeline application or a calendar application with a notification-affecting service resident on a wearable electronic device that has one or more user interfaces. FIGS. 3A and 3B and the description therefore provide at least one example of enabling the user of the wearable electronic device to monitor a time synchronous application with the notification-affecting service resident on a wearable electronic device.

FIG. 6 illustrates the method 600 having a second step 620 of executing the notification-affecting service on one or more processors the wearable electronic device. FIG. 1B and FIG. 2 and the descriptions therefore provide at least one example of executing the notification-affecting service on one or more processors the wearable electronic device.

FIG. 6 illustrates the method 600 having a third step 630 of evaluating multiple events listed, logged, or scheduled in the time synchronous application with the notification-affecting service. FIG. 6 also illustrates the method 600 having a fourth step 640 of independently using an intelligence engine to determine whether to automatically set a quiet time mode, thereby preventing one or more user-alerting actions respectively for one or more notifications. The descriptions for the schedule-aware quiet time mode and the calendar-aware quiet time mode provide 1) at least one example of evaluating multiple events listed, logged, or scheduled in the time synchronous application with the notification-affecting service and 2) at least one example of independently using an intelligence engine to determine whether to automatically set a quiet time mode.

In some embodiments, the software used to facilitate the algorithms discussed herein can be embodied onto a non-transitory machine-readable medium. A machine-readable medium includes any mechanism that stores information in a form readable by a machine (e.g., a computer). For example, a non-transitory machine-readable medium can include read only memory (ROM); random access memory (RAM); magnetic disk storage media; optical storage media; flash memory devices; Digital Versatile Disc (DVD's), EPROMs, EEPROMs, FLASH memory, magnetic or optical cards, or any type of media suitable for storing electronic instructions.

Note, an application herein described includes but is not limited to software applications, mobile apps, and programs that are part of an operating system application. Some portions of the detailed descriptions above are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like. These algorithms can be written in a number of different software programming languages such as C, C+, or other similar languages. Also, an algorithm can be implemented with lines of code in software, configured logic gates in software, or a combination of both. In an embodiment, the logic consists of electronic circuits that follow the rules of Boolean Logic, software that contain patterns of instructions, or any combination of both.

It should be borne in mind, however, that all of these and similar terms are to be associated with the appropriate physical quantities and are merely convenient labels applied to these quantities. Unless specifically stated otherwise as apparent from the above discussions, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers, or other such information storage, transmission or display devices.

While some specific embodiments of the design have been shown the design is not to be limited to these embodiments. For example, most functions performed by electronic hardware components can be duplicated by software emulation. Thus, a software program written to accomplish those same functions can emulate the functionality of the hardware components in input-output circuitry. The design is to be understood as not limited by the specific embodiments described herein, but only by scope of the appended claims.

What is claimed is:

1. An apparatus, comprising:
a notification-affecting service resident in a memory of a wearable electronic device that has one or more user interfaces configured to enable a user of the wearable electronic device to monitor a time synchronous application including a timeline application or a calendar application,
  i) where the wearable electronic device has one or more processors configured to execute the notification-affecting service resident in the memory;
  ii) where the notification-affecting service is configured to
    evaluate multiple events listed, logged, or scheduled in the time synchronous application and
    independently use an intelligence engine configured to determine whether to automatically set a quiet time mode, thereby preventing one or more user-alerting actions regarding a received notification selected from
      a haptic vibration,
      a visual effect on a display screen of the wearable electronic device, including turning on a back light of the wearable electronic device, and
      an audible sound effect emitted from the wearable electronic device;
  iii) where the received notification is received by a wireless receiver circuit of the wearable electronic device;
  iv) where the received notification is selected from any of the group consisting of
    calendar events notifications,
    incoming phone call notifications,
    mobile application generated notifications,
    SMS message notifications, and
    e-mail notifications;
  v) where portions of the notification-affecting service implemented in software are stored on the memory in an executable format by the one or more processors; and
  vi) where the notification-affecting service is configured to suppress the one or more user-alerting actions while the notifications are presented in a first time-ordered stack of notifications on the display screen in the quiet time mode.

2. The apparatus of claim 1,
where the notification-affecting service is configured to have at least three states of i) being on a scheduled setting, thereby affecting communication of any notifications based on a day of the week and time of day,
ii) being on a calendar aware setting, thereby affecting some or all the notifications, and
iii) being manually turned off allowing notifications to be freely communicated via the one or more user-alerting actions to a user of the wearable electronic device;

where the notification-affecting service is configured to be on calendar aware mode and enabled based on multiple events listed, logged, or scheduled for a calendar day; and where the notification-affecting service is configured to determine whether to automatically set the quiet time mode for multiple discreet blocks of time throughout the calendar day preventing the one or more user-alerting actions for at least some or all notifications in either the calendar aware setting or in the scheduled setting.

3. The apparatus of claim 1,
where the notification-affecting service is configured to present the notifications on the display screen while the quiet time mode is active, but
where the notification-affecting service prevents the one or more user-alerting actions when the quiet time mode is active; and
where the intelligence engine has logic trees for evaluating event types for events listed on the calendar application to determine whether a notification should be allowed to be communicated during a time period of any one of the events listed on the calendar application.

4. The apparatus of claim 1,
where the one or more user interfaces are configured to present multiple notification-service settings on the display screen to enable the user to choose one or more user-selectable settings selected from
i) a manual setting configured to enable the user to enable or disable the user-alerting actions as desired,
ii) a calendar-aware setting configured to automatically enter the quiet time mode during a time period for any one of the multiple events listed, logged, or scheduled in the time synchronous application including events on the calendar application, and
iii) a schedule-aware setting configured to enable the user to set different behaviors based on any of a time of day or day of a week or both of these for a work schedule including a work week schedule and a leisure schedule including a weekend schedule; and
where the one or more users interfaces are configured to present an option to the user to set both a start time and end time for the different behaviors.

5. The apparatus of claim 4,
where the one or more user interfaces are configured to further present an interruptions setting from the multiple notification-service settings on the display screen, and
where the interruptions setting is configured to enable the user to enable the user-alerting actions for phone calls when the user-alerting actions for other notifications are disabled.

6. The apparatus of claim 1,
where the notification-affecting service is configured to be in a calendar-aware setting; and
where the wearable electronic device is configured to automatically enter the quiet time mode during a time period for any one of the multiple events listed, logged, or scheduled in the time synchronous application including events on the calendar application or pins in the timeline application.

7. The apparatus of claim 6,
where the wearable electronic device is further configured to automatically not enter the quiet time mode during a time period for any one of the multiple events listed, logged, or scheduled in the time synchronous application including events on the calendar application or pins in the timeline application; and
where automatically entering or not entering the quiet time mode is dependent upon event types for events listed on the calendar application or pin types for pins in the timeline application.

8. The apparatus of claim 1,
where the notification-affecting service is configured to give granular control to a user of the notification-affecting service over the user-alerting actions for different notification-producing applications selected from the time synchronous application, a phone call application, a SMS message application, a social media site's application, and an e-mail application; and thus, allow user-alerting actions for at least one application selected from the time synchronous application, the phone call application, the SMS message application, the social media site's application, and the e-mail application, while also preventing the user-alerting actions for at least one application selected from the time synchronous application, the phone call application, the social media site's application, the SMS message application, and the e-mail application.

9. The apparatus of claim 8,
where the notification-affecting service is configured to give further granular control to the user over the user-alerting actions for the different notification-producing applications in accordance with the user's work week and leisure schedules.

10. The apparatus of claim 1,
where when a notification is received by the wireless receiver circuit of the wearable electronic device, then the notification-affecting service is configured to trigger a presentation to a user with one or more interfaces on the display screen of having an option of allowing the user to place the notification-affecting service in the quiet time mode.

11. The apparatus of claim 1,
where the notification-affecting service resident on the wearable electronic device is configured to automatically enter and exit multiple quiet time modes during the day based on either a time of day set in a scheduled setting or based on events logged on the time synchronous application without the user having to manually enter or exit out of any of the multiple quiet time modes.

12. The apparatus of claim 1,
where the notification-affecting service is configured to indicate the wearable electronic device is in the quiet time mode using an indicator on the display screen about the first time-ordered stack.

13. The apparatus of claim 1,
where the wearable electronic device is a smart watch,
where the notifications are further presented such that reminders for events on the calendar application or pins in the timeline application are presented in a second time-ordered stack of notifications on top of the first time-ordered stack, and where the notifications in the second time-ordered stack are automatically and individually removed from the second time-ordered stack after a pre-determined expiration period beginning from an event's start time in the calendar application or a pin's start time in the timeline application.

14. A method for affecting notifications on a wearable electronic device, comprising,
enabling a user of the wearable electronic device to monitor a time synchronous application including a timeline application or a calendar application with a notification-affecting service resident on the wearable electronic device that has one or more user interfaces,
i) where the wearable electronic device has one or more processors configured to execute the notification-affecting service resident in a memory of the wearable electronic device;
ii) where the notification-affecting service is configured to
evaluate multiple events listed, logged, or scheduled in the time synchronous application and
independently use an intelligence engine configured to determine whether to automatically set a quiet time mode, thereby preventing one or more user-alerting actions regarding a received notification selected from
a haptic vibration,
a visual effect on a display screen of the wearable electronic device, including turning on a back light of the wearable electronic device, and
an audible sound effect emitted from the wearable electronic device;
the received notification is received by a wireless receiver circuit of the wearable electronic device, where the received notification is selected from any of the group consisting of
calendar events notifications,
incoming phone call notifications,
mobile application generated notifications,
SMS message notifications, and
e-mail notifications;
iii) where portions of the notification-affecting service implemented in software are stored on the memory in an executable format by the one or more processors; and
iv) where the notification-affecting service is configured to suppress the one or more user-alerting actions while the notifications are presented in a first time-ordered stack of notifications on the display screen in the quiet time mode.

15. The method of claim 14,
where the notification-affecting service is configured to have at least three states of
i) being on a scheduled setting, thereby affecting communication of any notifications based on a day of the week and time of day,
ii) being on a calendar aware setting, thereby affecting some or all the notifications, and
iii) being manually turned off allowing notifications to be freely communicated via the one or more user-alerting actions to a user of the wearable electronic device;
where the notification-affecting service is configured to be on calendar aware mode and enabled based on multiple events listed, logged, or scheduled for a calendar day; and where the notification-affecting service is configured to determine whether to automatically set the quiet time mode for multiple discreet blocks of time throughout the calendar day preventing the one or more user-alerting actions for at least some or all notifications in either the calendar aware setting or in the scheduled setting.

16. The method of claim 14,
where the notification-affecting service is configured to present the notifications on the display screen while the quiet time mode is active, but
where the notification-affecting service prevents the one or more user-alerting actions when the quiet time mode is active; and
where the intelligence engine has logic trees for evaluating event types for events listed on the calendar application to determine whether a notification should be allowed to be communicated during a time period of any one of the events listed on the calendar application.

17. The method of claim 14,
enabling the user to choose one or more user-selectable notification-service settings in the one or more user interfaces on the display screen,
where the one or more user-selectable settings are selected from
i) a manual setting configured to enable the user to enable or disable the user-alerting actions as desired,
ii) a calendar-aware setting configured to automatically enter the quiet time mode during a time period for any one of the multiple events listed, logged, or scheduled in the time synchronous application including events on the calendar application, and
iii) a schedule-aware setting configured to enable the user to set different behaviors based on any of a time of day or day of a week or both of these for a work schedule including a work week schedule and a leisure schedule including a weekend schedule; and
where the one or more users interfaces are configured to present an option to the user to set both a start time and end time for the different behaviors.

18. The method of claim 17,
where the one or more user interfaces are configured to further present an interruptions setting from the multiple notification-service settings on the display screen, and
where the interruptions setting is configured to enable the user to enable the user-alerting actions for phone calls when the user-alerting actions for other notifications are disabled.

19. The method of claim 14,
where the notification-affecting service is configured to be in a calendar-aware setting; and
where the wearable electronic device is configured to automatically enter the quiet time mode during a time period for any one of the multiple events listed, logged, or scheduled in the time synchronous application including events on the calendar application or pins in the timeline application.

20. A system, comprising:
a mobile computing device;
a wearable electronic device configured to pair with the mobile computing device; and
a notification-affecting service resident in a memory of the wearable electronic device that has one or more user interfaces configured to enable a user of the wearable electronic device to monitor a time synchronous application including a timeline application or a calendar application, i) where the wearable electronic device has one or more processors configured to execute the notification-affecting service resident in the memory;

ii) where the notification-affecting service is configured to evaluate multiple events listed, logged, or scheduled in the time synchronous application and independently use an intelligence engine configured to determine whether to automatically set a quiet time mode, thereby preventing one or more user-alerting actions regarding a received notification selected from a haptic vibration, a visual effect on a display screen of the wearable electronic device, including turning on a back light of the wearable electronic device, and an audible sound effect emitted from the wearable electronic device;

iii) where the received notification is received by a wireless receiver circuit of the wearable electronic device;

iv) where the received notification is selected from any of the group consisting of calendar events notifications, incoming phone call notifications, mobile application generated notifications, SMS message notifications, and e-mail notifications;

v) where portions of the notification-affecting service implemented in software are stored on the memory in an executable format by the one or more processors; and vi) where the notification-affecting service is configured to suppress the one or more user-alerting actions while the notifications are presented in a first time-ordered stack of notifications on the display screen in the quiet time mode.

* * * * *